US009101935B2

(12) United States Patent
Park et al.

(10) Patent No.: US 9,101,935 B2
(45) Date of Patent: Aug. 11, 2015

(54) MICROFLUIDIC APPARATUS AND CONTROL METHOD THEREOF

(75) Inventors: Sang Bum Park, Hwaseong-si (KR); Na Hui Kim, Hwaseong-si (KR); Sang Hyun Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 224 days.

(21) Appl. No.: 13/604,045

(22) Filed: Sep. 5, 2012

(65) Prior Publication Data

US 2013/0065280 A1 Mar. 14, 2013

(30) Foreign Application Priority Data

Sep. 14, 2011 (KR) ........................ 10-2011-0092616

(51) Int. Cl.

*C12Q 1/68* (2006.01)
*C12P 19/34* (2006.01)
*G01N 21/75* (2006.01)
*G01N 21/66* (2006.01)
*B01L 3/00* (2006.01)

(52) U.S. Cl.

CPC ... *B01L 3/502769* (2013.01); *B01L 2200/0605* (2013.01); *B01L 2200/0673* (2013.01); *B01L 2200/141* (2013.01); *B01L 2300/0803* (2013.01); *B01L 2300/0864* (2013.01); *B01L 2400/0409* (2013.01); *B01L 2400/0677* (2013.01)

(58) Field of Classification Search

CPC .................. B01L 3/502769; B01L 2200/0605; B01L 2200/0673; B01L 2200/141; B01L 2300/0803; B01L 2300/0864; B01L 2300/0409; B01L 2300/0677

See application file for complete search history.

(56) References Cited

U.S. PATENT DOCUMENTS

2010/0015715 A1* 1/2010 Cho et al. ........................ 436/45

* cited by examiner

*Primary Examiner* — Young J Kim
(74) *Attorney, Agent, or Firm* — Sughrue Mion, PLLC

(57) ABSTRACT

A microfluidic apparatus having an additional chamber containing material configured to prevent cross contamination between reaction chambers contained therein, and a control method thereof are provided. The microfluidic apparatus includes a sample chamber configured to accommodate a sample, a plurality of reaction chambers each configured to accommodate a reagent, a distribution channel configured to distribute the sample into the plurality of reaction chambers, a mixture prevention chamber connected to the distribution channel and containing a mixture prevention material configured to prevent the reagents accommodated in the plurality of reaction chambers from being mixed with each other, and a valve disposed within the distribution channel and configured to open and close the distribution channel.

17 Claims, 8 Drawing Sheets

MICROFLUIDIC APPARATUS AND CONTROL METHOD THEREOF

CROSS-REFERENCE TO RELATED APPLICATION

This application claims priority from Korean Patent Application No. 10-2011-0092616, filed on Sep. 14, 2011 in the Korean Intellectual Property Office, the disclosure of which is incorporated herein by reference.

BACKGROUND

1. Field

Embodiments of the present invention relate to a microfluidic apparatus and a control method thereof, and more particularly, to a microfluidic apparatus capable of preventing cross contamination between reaction chambers, and a method thereof.

2. Description of the Related Art

A microfluidic apparatus is designed to manipulate a small quality of fluid such that a biological or chemical reaction is performed.

In general, a microfluidic structure for conducting an independent function in the microfluidic apparatus includes a chamber, which blocks a fluid, and a valve, which controls a channel through which a fluid flows and the flow of fluid, and is provided in a variety of combinations of such a chamber and valve. Lab-on-a-chip represents an apparatus configured to have a microfluidic structure disposed on a chip-shaped substrate to perform a test including a biological or chemical reaction on a small-sized chip, and to enable several steps of processes and manipulations. In order to transport a fluid in the microfluidic structure, a driving pressure is required, and a capillary force may be used as the driving pressure. In recent years, a disc-type microfluidic apparatus, which is configured to have a microfluidic structure disposed on a disc-shape platform and to perform a series of processes while moving a fluid by use of a centrifugal force, has been suggested.

When a polymerase chain reaction (PCR) is performed to amplify nucleic acid in the conventional microfluidic device, a reaction solution may be evaporated due to continuous thermal cycling reactions. The reaction solution evaporated from one reaction chamber may therefore be mixed with the reaction solution evaporated from another reaction chamber, thereby causing cross contamination between reaction chambers.

In addition, reaction solutions accommodated in reaction chambers may become separated from the respective reaction chambers due to shaking, vibration or an external impact. Such separated reaction solutions may then be mixed with another, thereby causing cross contamination between reaction chambers.

Such a cross contamination may degrade the reliability of nucleic acid reaction or other reactions that are expected at each reaction chamber.

SUMMARY

Exemplary embodiments provide a microfluidic apparatus having an additional chamber containing a material configured to prevent cross contamination between reaction chambers, and a control method thereof.

In accordance with one aspect of an exemplary embodiment, there is provided a microfluidic apparatus including a sample chamber, a plurality of reaction chambers, a distribution channel, a mixture prevention chamber and at least one valve. The sample chamber is configured to accommodate a sample. The plurality of reaction chambers is configured to accommodate a reagent. The distribution channel is configured to distribute the sample into one or more of the plurality of reaction chambers. The mixture prevention chamber is connected to the distribution channel and contains a mixture prevention material configured to prevent the reagents accommodated in the plurality of reaction chambers from being mixed with each other. The at least one valve is disposed within the distribution channel to open and close the distribution channel.

A first valve is disposed at a portion of the distribution channel connected to an outlet of the sample chamber and a second valve is disposed at a portion of the distribution channel connected to an outlet of the mixture prevention chamber.

The valve is a normally closed valve that keeps the distribution channel closed before energy is applied thereto.

The valve includes a mixture of a phase transition material and a heat generation fluid.

The phase transition material may be selected from one or more of wax, gel, and thermoplastic resin.

The heat generation fluid includes a carrier oil and heat generation particles dispersed in the carrier oil, wherein the heat generation particle is selected from the group consisting of metal oxides, polymer particles, quantum dots, and magnetic beads.

The microfluidic apparatus further includes an inlet channel configured to connect the distribution channel to the plurality of reaction chambers.

One end of the distribution channel includes a vent through which air is drained.

The mixture prevention material may be any material, which does not react with the reagent or the sample, and has a density smaller than the density of water.

The mixture prevention material is selected from the group consisting of liquid oil, liquid paraffin wax, and silicon oil.

The sample is a fluid including a nucleic acid molecule, and the reagent is a polymerase chain reaction solution including material needed for polymerase chain reaction amplification of the nucleic acid molecule.

In accordance with an aspect of another exemplary embodiment, there is provided a microfluidic system that includes the microfluidic apparatus, a rotary operation unit, an energy source and a controller. The rotary operation unit is configured to rotate the microfluidic apparatus. The energy source is configured to apply or irradiate energy onto the at least one valve of the microfluidic apparatus from outside the microfluidic apparatus. The controller is configured to transport a sample to the reaction chamber, to open the outlet of the mixture prevention chamber after the sample is transported to the reaction chamber, and to transport the mixture prevention material contained in the mixture prevention chamber to the distribution channel once the outlet of the mixture prevention chamber is opened.

The energy source is a laser light source.

The rotary operation unit is a spindle motor.

A movement of fluid within the microfluidic apparatus is achieved by centrifugal force that is generated as the microfluidic apparatus is rotated by the rotary operation unit.

If the sample is transported to the reaction chamber, the controller drives the rotary operation unit such that the valve, which closes the outlet of the mixture prevention chamber, moves to a position facing the energy source. Thereafter, the controller controls the energy source such that energy is irradiated onto the valve, thereby opening the outlet of the mixture prevention chamber.

If the outlet of the mixture prevention chamber is open, the controller thereafter drives the rotary operation unit such that the mixture prevention material contained in the mixture prevention chamber is transported into the distribution channel.

In accordance with an aspect of another exemplary embodiment, there is provided a method of controlling a microfluidic apparatus. The method includes transporting a sample to a reaction chamber. After transporting the sample to the reaction chamber, an outlet of a mixture prevention chamber of the microfluidic apparatus is opened. Upon the opening of the outlet of the mixture prevention chamber, a mixture prevention material contained in the mixture prevention chamber is transported to the distribution channel.

The opening of the outlet of the mixture prevention chamber of the microfluidic apparatus includes rotating a rotary operation unit such that a valve disposed within the outlet of the mixture prevention chamber is moved to a position facing an energy source, and the energy source is driven such that energy is irradiated onto the valve after the valve is moved to the position facing the energy source, thereby opening the outlet of the mixture prevention chamber.

The transporting of the mixture prevention material includes rotating the rotary operation unit such that the mixture prevention material is transported into the distribution channel.

As described above, cross contamination between a plurality of reaction chambers may be prevented, thereby improving the efficiency and the reproducibility of the biochemical reactions that are expected within each reaction chamber.

BRIEF DESCRIPTION OF THE DRAWINGS

The above and/or other aspects will become apparent and more readily appreciated from the following description of embodiments, taken in conjunction with the accompanying drawings of which.

DETAILED DESCRIPTION

Figure 1:
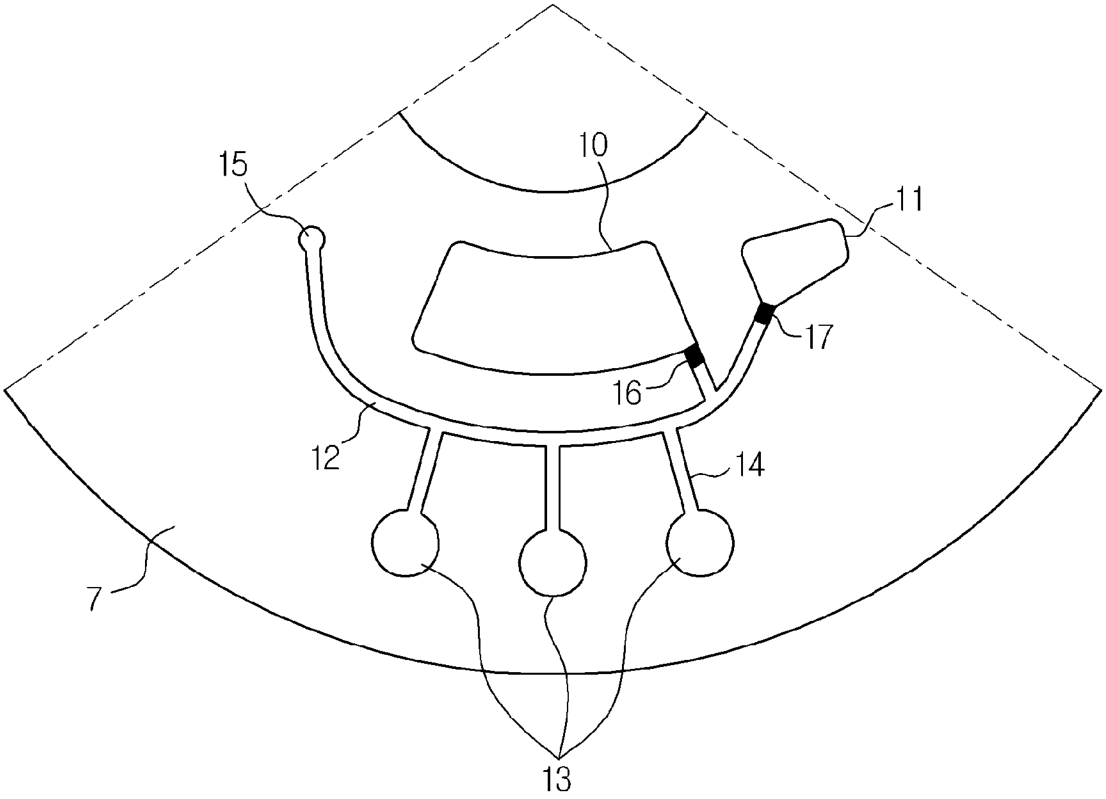
FIG. 1 is a view illustrating the structure of a microfluidic apparatus according to an exemplary embodiment.

Reference will now be made in detail to the embodiments, examples of which are illustrated in the accompanying drawings, wherein like reference numerals refer to like elements throughout.

Also, structures such as a chamber or a channel can be simplified in shape, and the proportion thereof can be exaggerated for the purpose of convenience and clarity. With regard to expressions such as a "microfluidic device" and a "micro-particle," the term "micro-" is not used as a limited metric meter, but is used in representing the opposite to "macro-".

FIG. 1 is a view illustrating a structure of a microfluidic apparatus according to an exemplary embodiment.

Referring to FIG. 1, a microfluidic apparatus according to an embodiment of the present disclosure includes a platform 7, a sample chamber 10 configured to accommodate a sample 8, a distribution channel 12 configured to distribute the sample 8 transported from the sample chamber 10 into a plurality of reaction chambers 13, the plurality of reaction chambers 13, each configured to accommodate the distributed sample 8 and to contain a reagent which reacts with the sample 8, and a mixture prevention chamber 11 connected to the distribution channel 12 and configured to contain a mixture prevention material 9 that is provided to the distribution channel 12 to prevent a cross contamination among the plurality of reaction chambers 13.

The platform 7 may include a disc-shape platform. The shape of the platform 7 is not limited thereto. The platform 7 may be formed using plastics, such as acryl, that are easy to mold and have biologically inert superficial properties. The material of the platform 7 is not limited thereto, and may be implemented using various other materials having chemical and biological stability, optical transparency, and mechanical workability.

In an exemplary embodiment, the materials from which the platform 7 may be formed include, but are not limited to, plastic, PMMA (Polymethylmethacrylate), glass, mica, silica, material of a silicon wafer, and plastic. For the sake of economic efficiency and plasticity, plastic may be used.

Plastics from which the platform 7 may be formed include, but are not limited to, polypropylene, polyacrylate, polyvinyl alcohol, polyethylene, polymethylmethacrylate (PMMA), polycarbonate, etc.

In addition, the platform 7 may be provided in the form of a plate including a plurality of layers. After various engraved structures, corresponding to chambers, channels, etc., are formed at facing surfaces of the layers, the layers are bonded to each other, thereby providing spaces and channels within the platform 7.

The bonding of layers may be achieved by various methods, such as use of an adhesive, double-side adhesive tape, ultrasonic welding, or laser welding.

The platform 7 may be provided with at least one microfluidic structure. For example, the platform 7 may be divided into a plurality of regions, and within each of the regions, one or more microfluidic structures that independently operate may be provided, respectively.

The term "microfluidic structure" does not denote a particular structure, but commonly designates a structure that includes a plurality of chambers and channels and at least one valve to control fluid flow. Accordingly, the term "microfluidic structure" may be composed of individual units, each performing a different function according to the disposition of the chamber, the channel and the valves, and according to the type of material contained in the unit.

When centrifugal force is used as the driving pressure for fluid transportation, the platform 7 may be provided in a disc shape. However, the shape of the platform 7 is not limited to a complete disc shape. For example, the platform 7 may be provided in a sector form that is mounted on a rotatable frame for rotation.

The sample chamber 10 provides a space that may accommodate the sample 8 in a fluidic state.

The sample chamber 10 includes a sample injection part (not shown) for the injection of the sample 8 and an accommodation part (not shown) for accommodating the sample. A structure serving as a capillary valve may be formed between the sample injection part and the accommodation part to allow the sample to flow to the accommodation part by the injection pressure of the sample 8, while preventing the sample from flowing backward via capillary force to the sample injection part. That is, the structure allows the sample 8 to pass therethrough only when a pressure of more than a predetermined level is applied.

An outlet of the sample chamber 100 configured to drain the sample is connected to the distribution channel 12. A valve 16 is disposed within the outlet of the sample chamber 100 to control the flow of the sample 8. The flow of the sample 8 through the channel is controlled by opening/closing of the valve 16. The valve 16 may be provided in various shapes of microfluidic valves.

Figure 5A:
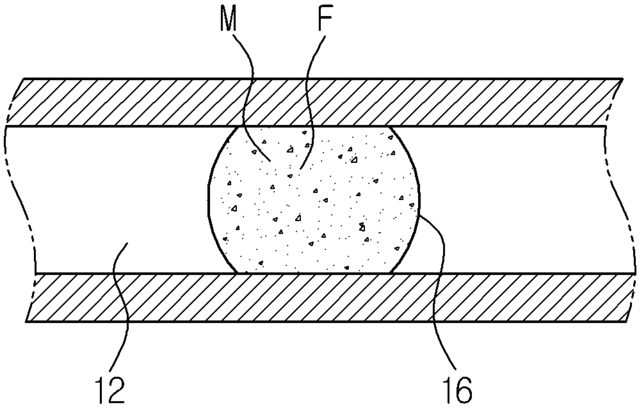
FIGS. 5A and 5B are cross-sectional views illustrating the structure of a valve according to an exemplary embodiment.
Figure 5B:
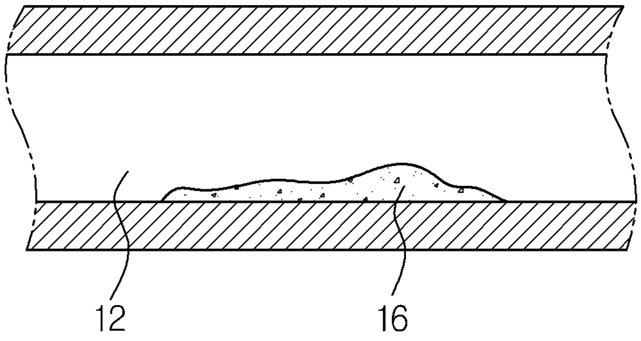

For example, with reference to FIGS. 5A and 5B, the valve 16 may be a normally closed valve that blocks the channel 12 to prevent a fluid from flowing. In detail, the valve may be manufactured by mixing a phase transition material M with a heat generation fluid F. The phase transition material M may be wax, gel, or thermoplastic resin. The wax may be formed using paraffin wax. Exemplary gels include, but are not limited to, polyacrylamide, polyacrylates, polymethacrylates, or polyvinylamides. Exemplary thermoplastic resins include, but are not limited to, COO (cyclic olefin copolymer), PMMA (polymethylmethacrylate), PC (polycarbonate), PS (polystyrene), POM (polyoxymethylene), PFA (perfluoralkoxy), PVC (polyvinylchloride), PP (polypropylene), PET (polyethylene terephthalate), PEEK (polyetheretherketone), PA (polyamide), PSU (polysulfone), or PVDF (polyvinylidene fluoride). The heat generation fluid F includes a carrier oil having hydrophobic property and micro heat generation particles dispersed within the carrier oil. The micro heat generation particles may be in the range of several tens or several hundreds of nanometers in diameter. When energy is provided through a predetermined method, for example, laser beam radiation, the micro heat generation particle rapidly absorbs energy and generates heat. The micro heat generation particle may be a fine particle of a metal oxide having ferromagnetism. Thus, when energy is provided to the valve 16 through, e.g., a laser beam, the solid valve melts to open the channel.

As the valve 16 is given energy from outside to open the channel, the sample 8 accommodated in the sample chamber 10 is transported to the distribution channel 12 by the driving pressure implemented by the centrifugal force. The sample 8 accommodated in the sample chamber 10 may be a fluid including a nucleic acid.

The distribution channel 12 is connected to the sample chamber 10, and is disposed at a position farther away from the center of the platform 7 than the position of the sample chamber 10.

The distribution channel 12 extends along the periphery of the platform 7 while having a curvature similar to that of the periphery of the platform 7. The distribution channel 12 is designed to provide the same fluid resistance throughout the overall area of the distribution channel 12.

A vent 15 is formed at one end of the distribution channel 12 to drain air therefrom. As the air within the channel is drained, the fluid is transported through the channel 12. The end of the distribution channel 12 having the vent 15 may be bent toward the center of the platform 7 at a predetermined angle.

The distribution channel 12 is connected to the plurality of reaction chambers 13 such that the sample departing from the sample chamber 10 is transported to each of the respective reaction chambers 13.

The plurality of reaction chambers 13 are connected to the distribution channel 12, and accommodate the sample 8 distributed from the distribution channel 12 while being disposed at a position farther away from the center of the platform 7 than the position of the distribution channel 12.

Each of the plurality of reaction chambers 13 may include a reagent that is used for a biochemistry reaction with the sample 8. The reagents included in the respective reaction chambers 13 may be the same material for the same reaction or the different materials for different reactions.

For example, the plurality of reaction chambers 13 may be chambers configured to perform a Polymerase Chain Reaction (PCR) for amplification of a nucleic acids, and the reagent included in each of the reaction chambers 13 may be the PCR reagent including the material needed to amplify a nucleic acid molecule. The reaction chamber 13 accommodates a fluid which is transported from the sample chamber 10 via the distribution channel 12, and includes a nucleic acid molecule. As the fluid including the nucleic acid molecule is accommodated in the reaction chamber 13, the fluid is mixed with the PCR reagent in the reaction chamber 13, bringing out a PCR amplification reaction. Herein, the PCR reagent may be a reagent for performing real-time PCR.

Each of the plurality of reaction chambers 13 is connected to inlet channels 14 that are diverged from the distribution channel 12 while radially extending outward, so that the reaction chambers 13 receive the sample 8 distributed from the distribution channel 12. That is, the inlet channel 14 configured to connect the plurality of reaction chambers 13 to the distribution channel 12 is disposed between the distribution channel 12 and the reaction chamber 13. The cross section of the inlet channel 14 may have a diameter smaller than that of the reaction chamber 14.

The mixture prevention chamber 11 is disposed at a position closer to the center of the platform 7 than the position of the distribution channel 12. The mixture prevention chamber 11 accommodates a mixture prevention material 9. Provided at the outlet of the mixture prevention chamber 11 is a valve 17 that is configured to control the flow of the mixture prevention material 9. The valve 17 opens or closes the channel, thereby controlling the flow of the mixture prevention material 9 passing through the channel. The valve may be implemented using various types of micro-fluid valves.

For example, the valve 17 may be a normally closed valve that blocks the channel to prevent a fluid from flowing. Since the description of the valve 17 is identical to the description of the valve 16 of the sample chamber 10, the detailed description of the valve 17 is omitted.

As the valve 17 is given energy from outside to open the channel, the mixture prevention material 9 accommodated in the mixture prevention chamber 11 is transported to the distribution channel 12 by the driving pressure implemented by the centrifugal force.

After the valve 16 disposed at the outlet of the sample chamber 10 opens to transport the sample to the reaction chamber 13, the valve 17 disposed at the outlet of the mixture prevention chamber 11 is configured to open the channel by receiving energy from outside.

As the channel is opened, the mixture prevention material 9 is introduced to the distribution channel 12, and the distribution channel 12 is filled with the mixture prevention material 9. The mixture prevention material 9 filled in the distribution channel 12 physically blocks the mixture of the sample 8 and the reagent in the reaction chamber 13 from flowing backward to the distribution channel 12, thereby preventing any cross contamination among the sample/reagent mixtures within each of the plurality of the reaction chambers 13 due to an external force, a vibration, or a shaking.

In a case that the chambers of the plurality of reaction chambers 13 are configured to perform a PCR amplification reaction, a PCR reagent may be evaporated due to continuous thermal cycling reactions performed at a high temperature. However, the mixture prevention material 9 filled in the distribution channel 12 physically blocks the evaporated reagent from flowing backward into the distribution channel 12, thereby preventing any cross contamination between the reaction chambers 13.

As should be understood, the mixture prevention material 9 should not mix with the sample and the reagent within the reaction chamber 13, should not inhibit a reaction from occurring. Accordingly, in various embodiments, the mixture prevention material 9 is not reactive with the sample and/or the reagent, and has a density lower than those of the sample and the reagent. When the reaction chamber 13 is a chamber for PCR amplification reactions, the mixture prevention material 9 should have a boiling point of 90 degrees or higher since the heat cycling reactions of PCR occur at high temperatures. For example, the mixture prevention material 9 may be liquid oil, liquid paraffin wax, or silicon oil.

Figure 2:
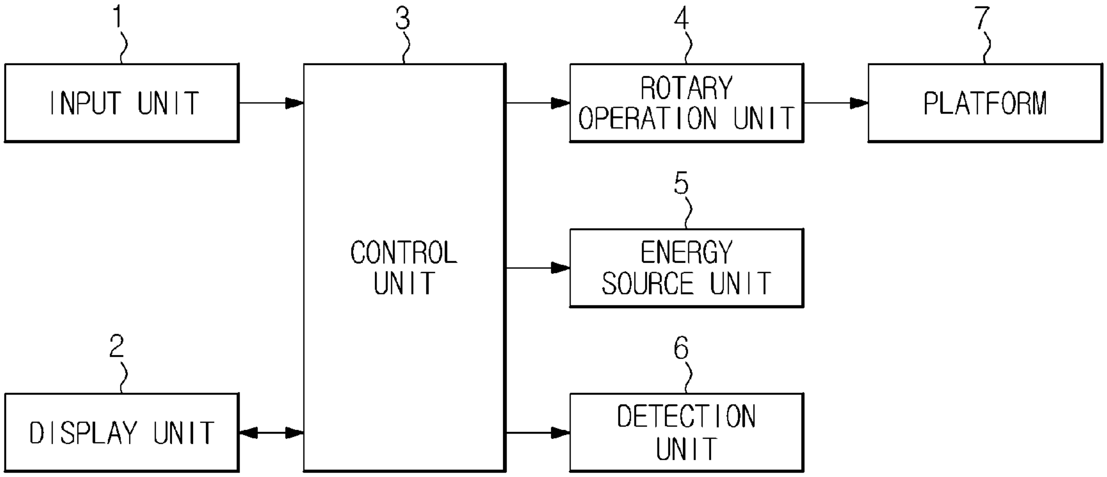
FIG. 2 is a block diagram illustrating the configuration of a microfluidic system according to an exemplary embodiment.

FIG. 2 is a block diagram illustrating the configuration of a microfluidic system according to an exemplary embodiment.

Referring to FIG. 2, the microfluidic system includes an input unit 1, a display unit 2, a control unit 3 (i.e., controller), a rotary operation unit 4, an energy source unit 5 (i.e., energy source), and a detection unit 6. The input unit 1 is configured to receive a command input by a user. The display unit 2 is configured to display various information about the microfluidic system to the user. The control unit 3 is configured to control the overall operations and functions of the microfluidic system according to the commands of the input unit 1. The rotary operation unit 4 is configured to rotate the microfluidic apparatus while supporting the microfluidic apparatus. The energy source unit 5 is disposed outside the microfluidic apparatus and configured to apply energy to the valves 16 and 17 of the microfluidic apparatus. The detection unit 6 is configured to detect the results of various reactions occurring within the microfluidic apparatus.

The rotary operation unit 4 rotates the microfluidic apparatus by use of a spindle motor. The rotary operation unit 4 repeats a rotation and stops by receiving a signal output from the control unit 3, thereby generating the centrifugal force needed to transport a fluid within the microfluidic apparatus, and/or moving various structures of the microfluidic apparatus to desired positions.

The energy source unit 5 is disposed outside the microfluidic apparatus to irradiate energy onto the valves 16 and 17. The energy source unit 5 may be a light source configured to radiate visible light or infrared light. In various embodiments, the energy source unit 5 may be a light-emitting diode or a Xenon lamp. In other embodiments, the energy source unit 5 may be a laser light source to radiate a laser beam. The laser light source is provided with a laser diode to radiate a laser beam toward the solid valve(s). Thus, when the laser light source radiates a laser beam toward the valve(s), the valve(s) is melted by the energy provided by the laser beam, thereby opening or closing the channel.

The energy source unit 5 may be provided at an upper surface thereof with a movable unit (not shown) that enables the energy source unit 5 to move in a radial direction in relation to the microfluidic apparatus. The movable unit may include a motor, which provides a driving force for movement of the energy source unit 5, and a gear unit. The gear unit, in conjunction with the rotation of the motor, moves the energy source unit 5 to a position facing a valve to be opened within a channel within the microfluidic device.

That is, when a solid (i.e., closed) valve of a channel is to be opened, the microfluidic device is rotated by the rotary operation unit 4 such that the valve is moved into radial alignment with the energy source unit 5, and the energy source unit 5 moves in a radial direction of the microfluidic apparatus to a position facing the valve to irradiate energy onto the valve. The axial directional movement of the microfluidic apparatus in combination with the radial directional movement of the energy source unit 5 enables energy to be precisely irradiated onto the valve of channel that is to be opened.

The detection unit 6 is disposed outside the microfluidic structure, and configured to detect results of reactions within the reaction chambers 13. The detection unit 6 may include a light-emitting unit (i.e., light emitter) and a light receiving unit (i.e., light receiver) which is provided to correspond to the light-emitting unit to receive the light passing through the reaction chamber 13.

The light-emitting unit is a light source configured to flicker at a predetermined frequency. The light-emitting unit may include a semiconductor light emitting device, such as a laser diode (LD), and/or a gas emission lamp, such as a Halogen lamp or a Xenon lamp.

The light-receiving unit is configured to generate an electric signal according to the intensity of incident light. For example, the light-receiving unit may include a depletion layer photo diode, an avalanche photo diode (APD), or a photomultiplier tubes (PMT). The light-emitting unit and the light-receiving unit of the detection unit 6 may be vertically disposed opposite to each other while interposing the microfluidic apparatus therebetween. A light path may be adjusted through a reflection mirror or a light guide member.

In order to move the sample 8 accommodated in the sample chamber 10 to the reaction chamber 13, the control unit 3 controls the operation of the rotary operation unit 4 and the light source unit 5 such that the valve 16, which keeps the outlet of the sample chamber 10 closed, is moved to a position facing the energy source unit 5.

As the valve 16 moves to the position facing the energy source unit 5, the control unit 3 operates the energy source unit 5 to irradiate energy onto the valve 16 such that the valve 16 is melted, thereby opening the outlet of the sample chamber 10.

Figure 3A:
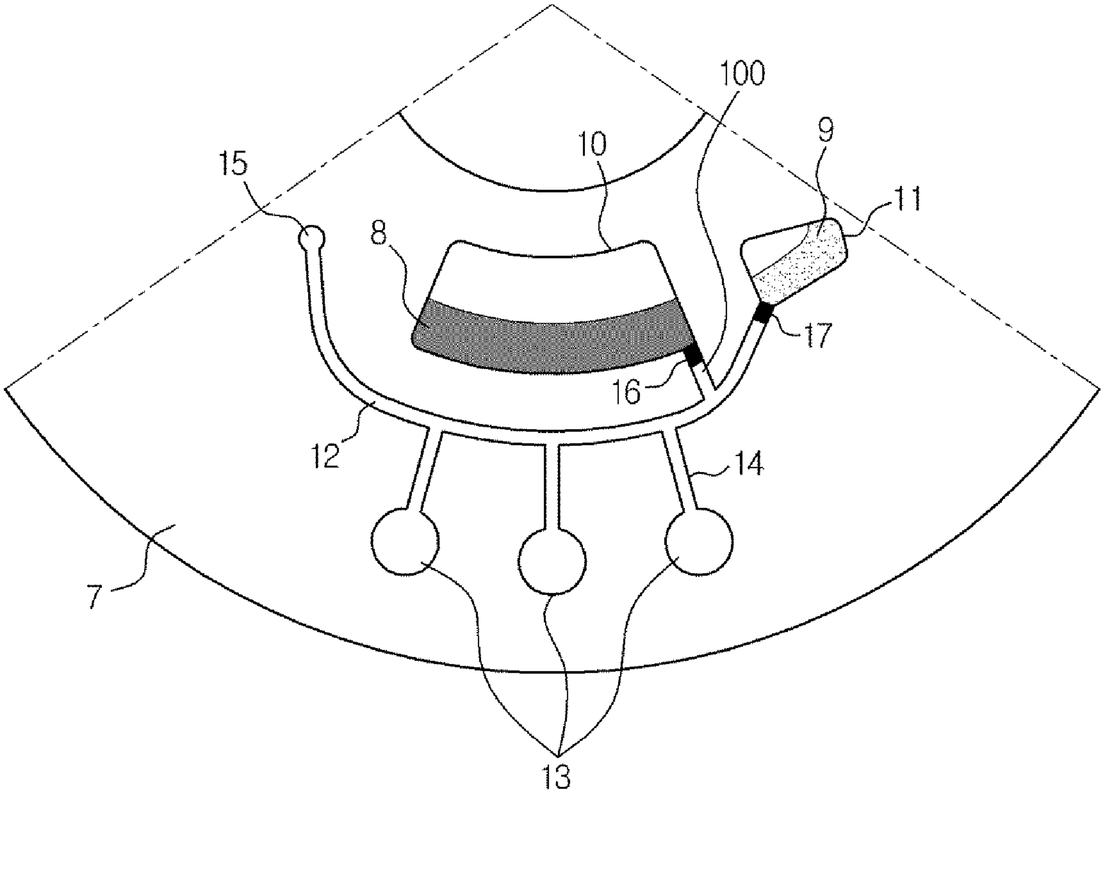
FIGS. 3A to 3C are views illustrating the fluid flow in the microfluidic apparatus according to an exemplary embodiment.
Figure 3B:
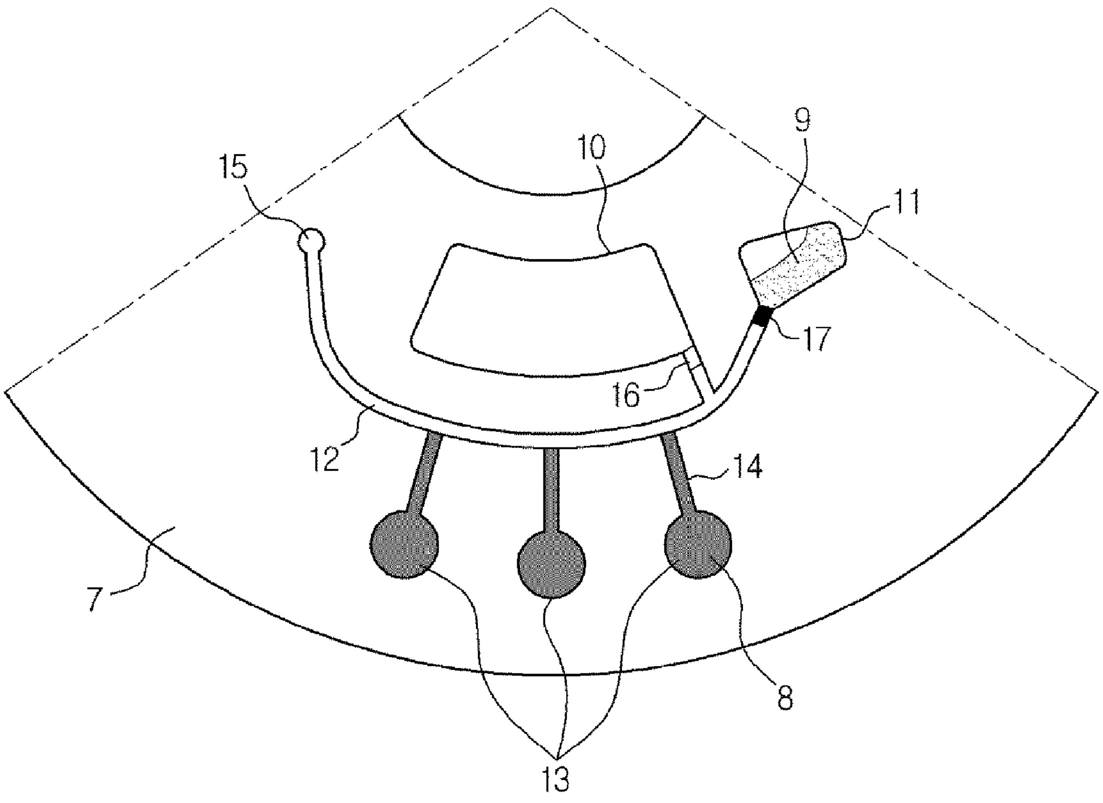

After opening the outlet of the sample chamber 10, the control unit 3 drives the rotary operation unit 4 to generate centrifugal force such that the sample 8 is introduced into the plurality of reaction chambers 13. FIG. 3A is a view illustrating a state in which the sample 8 and the mixture prevention material 9 are accommodated in the sample chamber 10 and the mixture prevention chamber 11, respectively. The valves 16 and 17 are disposed at the outlets of the sample chamber 10 and the mixture prevention chamber 11, respectively, closing the respective outlets. FIG. 3B illustrates a state in which the valve 16 is melted as described above to open the outlet, and thus the sample 8 is distributed to the respective reaction chambers 13 via the distribution channel 12. However, in this case, the outlet of the mixture prevention chamber is kept closed.

Once the sample 8 is transported to the respective reaction chambers 13 via the distribution channel 12, the control unit 3 drives the rotary operation unit 4 such that the valve 17 is moved to a position facing the energy source unit 5. The control unit 3 then operates the energy source unit 5 to irradiate energy onto the valve 17, thereby opening the outlet of the mixture prevention chamber 11.

After the outlet of the mixture prevention chamber 11 is open, the control unit 3 drives the rotary operation unit 4 so that the mixture prevention material 9 is transported to the distribution channel 12.

Figure 3C:
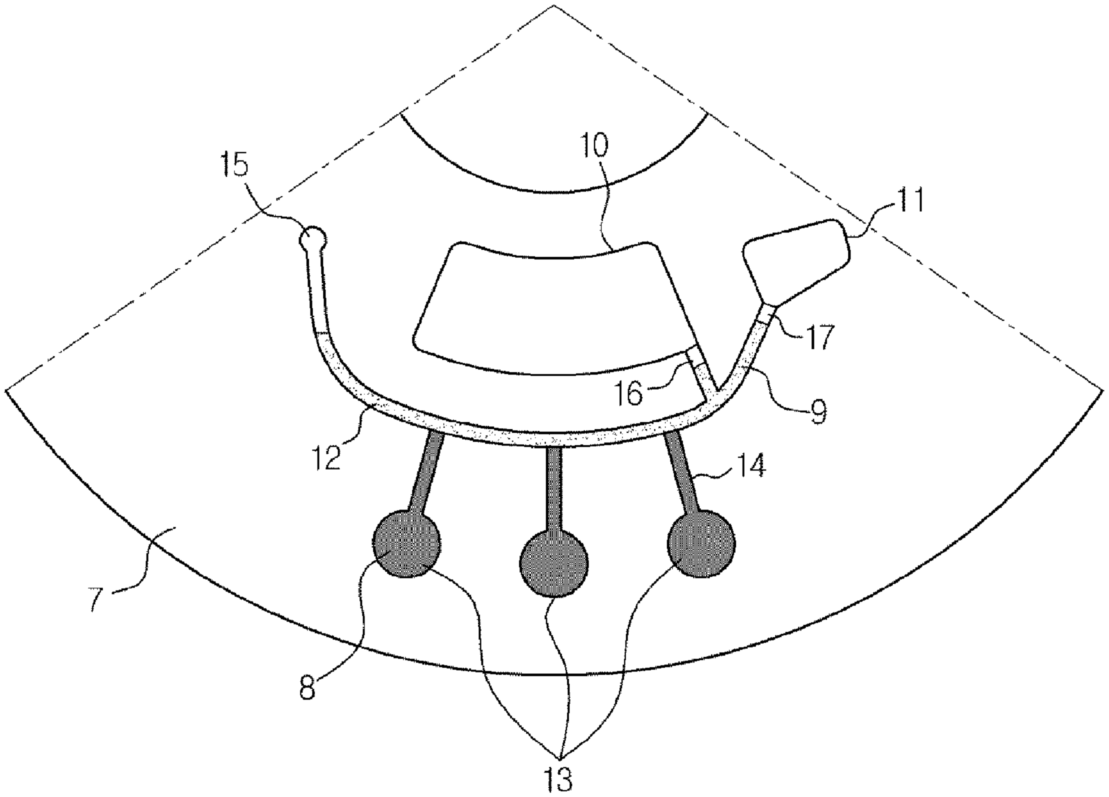

FIG. 3C is a view illustrating a state in which when the outlet of the mixture prevention chamber 11 is open and the mixture prevention material 9 has been transported to and filled the distribution channel 12. Thus, the mixture prevention material 9 physically blocks the sample 8 and the reagent that react within the reaction chamber 13 from flowing backward into the distribution channel 12, thereby lowering the chance of cross contamination among the plurality of reaction chambers 13.

Figure 4:
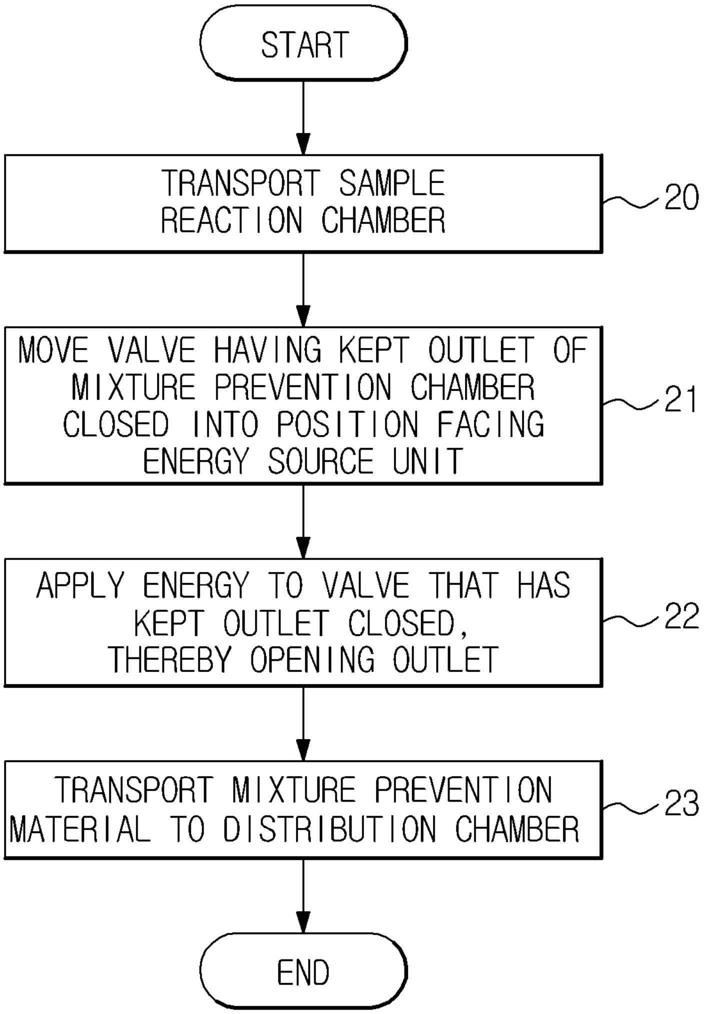
FIG. 4 is a flowchart showing a control method of a microfluidic apparatus according to an exemplary embodiment.

FIG. 4 is a flowchart showing a control method of a microfluidic apparatus according to an exemplary embodiment.

Referring to FIG. 4, the control unit 3 transports a sample 8 accommodated in the sample chamber 10 to the reaction chamber 13 (20).

The control unit 3 drives the rotary operation unit 4 such that the valve 16, having kept the outlet of the sample chamber 10 closed, is moved into radial alignment with the energy source unit 5.

As the valve 16 is moved into radial alignment with the energy source unit 5, the control unit 3 checks whether the valve 16 is disposed at a position facing the energy source unit 5, and if the valve 16 is not positioned facing the energy source unit 5, operates a movable unit (not shown) that enables the energy source unit 5 to move in a radial direction in relation to the microfluidic apparatus such that the valve 16 and the energy source unit 5 face each other.

After the energy source 5 and the valve 16 are positioned facing each other, the control unit 3 controls the energy source 5 to irradiate energy onto the valve 16 such that the valve 16 is melted, thereby opening the outlet of the sample chamber 10. As described above, the energy source unit 5 may be a laser light source unit configured to irradiate a laser beam. The valve may be formed using a phase transition material M and a heat generation fluid F.

As the outlet of the sample chamber 10 is opened, the control unit 3 drives the rotary operation unit 4. The resulting centrifugal force generated serves as a driving force for transporting the sample 8. Accordingly, the sample 8 is distributed to each of the respective reaction chambers 13 via the distribution channel 12.

After the sample is transported to the respective reaction chambers 13, the control unit 3 moves the valve 17, which in solid form keeps the outlet of the mixture prevention chamber 11 closed, to a position facing the energy source unit 5 (21).

The control unit 3 drives the rotary operation unit 4 such that the valve 17 is moved into radial alignment with the energy source unit 5.

After the valve 17 is moved into radial alignment with the energy source unit 5, the control unit 3 checks whether the valve 17 is positioned facing the energy source unit 5, and if the valve 17 is not positioned facing the energy source unit 5, operates a movable unit (not shown) that enables the energy source unit 5 to move in a radial direction in relation to the microfluidic apparatus such that the valve 17 and the energy source unit 5 face each other.

After the energy source 5 and the valve 17 are positioned facing each other, the control unit 3 controls the energy source 5 to irradiate energy onto the valve 17 such that the valve 17 is melted, thereby opening the outlet of the mixture prevention chamber 11 (22).

As the outlet of the mixture prevention chamber 11 is opened, the control unit 3 drives the rotary operation unit 4 (23). The resulting centrifugal force generated serves as a driving force for transporting the mixture prevention material 9. Accordingly, the mixture prevention material 9 is distributed into the distribution channel 12, thereby filling the distribution channel 12. The mixture prevention material 9 filled in the distribution channel 12 physically blocks the sample 8 and the reagent that react in a biochemistry reaction in the reaction chamber 13 from flowing backward into the distribution channel 12, thereby lowering the chances of cross contamination among the plurality of reaction chambers 13.

Although exemplary embodiments have been shown and described, it should be appreciated by those skilled in the art that changes may be made in these embodiments without departing from the principles and spirit of the disclosure, the scope of which is defined in the claims and their equivalents.

What is claimed is:

1. A microfluidic apparatus comprising:

a sample chamber configured to accommodate a sample;

a plurality of reaction chambers each configured to accommodate a reagent;

a distribution channel configured to distribute the sample from the sample chamber into the plurality of reaction chambers;

a mixture prevention chamber connected to the distribution channel and containing a mixture prevention material configured to prevent the reagents accommodated in the plurality of reaction chambers from being mixed with each other; and at least one valve disposed within the distribution channel and configured to open and close the distribution channel.

2. The microfluidic apparatus of claim 1, wherein the at least one valve comprises a first valve disposed at a portion of the distribution channel connected to an outlet of the sample chamber and a second valve is disposed at a portion of the distribution channel connected to an outlet of the mixture prevention chamber.

3. The microfluidic apparatus of claim 1, wherein the at least one valve is a normally closed valve that keeps the distribution channel closed before energy is applied thereto.

4. The microfluidic apparatus of claim 1, wherein the at least one valve comprises a mixture of a phase transition material and a heat generation fluid.

5. The microfluidic apparatus of claim 4, wherein the phase transition material is selected from the group consisting of wax, gel, and thermoplastic resin.

6. The microfluidic apparatus of claim 4, wherein the heat generation fluid comprises a carrier oil and heat generation particles dispersed within the carrier oil, and wherein the heat generation particles are selected from the group consisting of metal oxides, polymer particles, quantum dots, and magnetic beads.

7. The microfluidic apparatus of claim 1, further comprising at least one inlet channel configured to connect the distribution channel to the plurality of reaction chambers.

8. The microfluidic apparatus of claim 1, further comprising a vent disposed at one end of the distribution channel and through which air is drained.

9. The microfluidic apparatus of claim 1, wherein the mixture prevention material is a material that does not react with the reagent and the sample and has a density smaller than a density of water.

10. The microfluidic apparatus of claim 1, wherein the mixture prevention material is selected from the group consisting of liquid oil, liquid paraffin wax, and silicon oil.

11. The microfluidic apparatus of claim 1, wherein the sample is a fluid comprising a nucleic acid molecule, and the reagent is a polymerase chain reaction solution for polymerase chain reaction of the nucleic acid molecule.

12. A microfluidic system comprising:

the microfluidic apparatus of claim 1;

a rotary operation unit configured to rotate the microfluidic apparatus;

an energy source configured to apply energy to the at least one valve of the microfluidic apparatus from outside the microfluidic apparatus; and a controller configured to control rotation of the rotary operation unit, thereby transporting a sample to the reaction chamber, to open the outlet of the mixture prevention chamber if the sample is transported to the reaction chamber and to transport the mixture prevention material contained in the mixture prevention chamber to the distribution channel when an outlet of the mixture prevention chamber is open.

13. The microfluidic system of claim 12, wherein the energy source is a laser light source.

14. The microfluidic system of claim 12, wherein the rotary operation unit is a spindle motor.

15. The microfluidic system of claim 12, wherein movement of fluid within the microfluidic apparatus is achieved by centrifugal force that is generated as the microfluidic apparatus is rotated by the rotary operation unit.

16. The microfluidic system of claim 12, wherein the controller is configured to, if the sample is transported to the reaction chamber, drive the rotary operation unit to move a valve disposed at the outlet of the mixture prevention chamber to a position facing the energy source, and control the energy source to apply energy to the valve, thereby opening the outlet of the mixture prevention chamber.

17. The microfluidic system of claim 12, wherein the controller is configured to, if the outlet of the mixture prevention chamber is open, drive the rotary operation unit such that the mixture prevention material contained in the mixture prevention chamber is transported into the distribution channel.

* * * * *